US008415292B2

(12) United States Patent
Madden et al.

(10) Patent No.: US 8,415,292 B2
(45) Date of Patent: Apr. 9, 2013

(54) COMPOSITIONS AND METHODS FOR INHIBITING THE INTERACTION BETWEEN CFTR AND CAL

(75) Inventors: Dean Madden, Hanover, NH (US); Patrick R. Cushing, East Thetford, VT (US); Prisca Boinguérin, Berlin (DE); Rudolf Volkmer, Nordwestuckermark (DE); Lars Vouilleme, Berlin (DE)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/124,470

(22) PCT Filed: Oct. 20, 2009

(86) PCT No.: PCT/US2009/061246
§ 371 (c)(1),
(2), (4) Date: Apr. 15, 2011

(87) PCT Pub. No.: WO2010/048125
PCT Pub. Date: Apr. 29, 2010

(65) Prior Publication Data
US 2011/0201544 A1     Aug. 18, 2011

Related U.S. Application Data

(60) Provisional application No. 61/107,438, filed on Oct. 22, 2008.

(51) Int. Cl.
*A61K 35/00* (2006.01)
(52) U.S. Cl. ......... 514/1.8; 530/327; 530/328; 530/329; 530/326; 514/21.4; 514/21.5; 514/21.6; 514/21.7; 514/21.8
(58) Field of Classification Search .............. 514/1.8
See application file for complete search history.

(56) References Cited

U.S. PATENT DOCUMENTS

2005/0196754 A1    9/2005  Drmanac et al. ........... 435/6.11
2005/0282743 A1*  12/2005  Lu et al. ........................ 514/12
2007/0044171 A1    2/2007  Kovalic et al. ................. 800/278
2007/0061916 A1*   3/2007  Kovalic et al. ................. 800/278
2008/0069838 A1*   3/2008  Peiris et al.

OTHER PUBLICATIONS

Schulz et al., Clinical Cancer Research (1998) 4(9), 2047-2052.*
Cheng et al. "A Golgi-associated PDZ Domain Protein Modulates Cystic Fibrosis Transmembrane Regulator Plasma Membrane Expression" The Journal of Biological Chemistry 2002 277(5):3520-3529.
Guerra et al. "Na+/H+Exchanger Regulatory Factor Isoform 1 Overexpression Modulates Cystic Fibrosis Transmembrane Conductance Regulator (CFTR) Expression and Activity in Human Airway 16HBE14o- Cells and Rescues ΔF508 CFTR Functional Expression in Cystic Fibrosis Cells" The Journal of Biological Chemistry 2005 280(49):40925-40933.
Guggino, W.B. and Stanton, B.A. "New Insights into Cystic Fibrosis: Molecular Switches that Regulate CFTR" Nature Reviews Molecular Cell Biology 2006 7(6):426-436.
Li, C. and Naren, A.P. "Macromolecular Complexes of Cystic Fibrosis Transmembrane Conductance Regulator and its Interacting Partners" Pharmacology & Therapeutics 2005 108(2):208-223.
Wolde et al. "Targeting CAL as Negative Regulator of ΔF508-CFTR Cell-Surface Expression" The Journal of Biological Chemistry 2007 282(11):8099-8109.
Bossard et al. "NHE-RF1 Protein Rescues ΔF508-CFTR Function" American Journal of Physiology—Lung Cellular and Molecular Physiology 2007 292: L1085-L1094.
Cushing et al. "The Relative Binding Affinities of PDZ Partners for CFTR: a Biochemical Basis for Efficient Endocytic Recycling" Biochemistry 2008 47(38):10084-10098.
International Search Report from PCT/US2009/061246, Aug. 25, 2010, PCT.
International Preliminary Report on Patentability from PCT/US2009/061246, May 5, 2011, PCT.

* cited by examiner

*Primary Examiner* — Karlheinz R Skowronek
*Assistant Examiner* — Catherine Mader
(74) *Attorney, Agent, or Firm* — Licata & Tyrrell P.C.

(57) ABSTRACT

The present invention features compositions and methods for increasing the cell surface expression of degradation-prone CFTR proteins and preventing or treating cystic fibrosis. The invention provides peptides and peptidomimetics that selectively inhibit the interaction between CAL and mutant CFTR proteins, thereby stabilizing the CFTR and facilitating transport of the same to the cell surface.

6 Claims, No Drawings

US 8,415,292 B2

COMPOSITIONS AND METHODS FOR INHIBITING THE INTERACTION BETWEEN CFTR AND CAL

This application is the National Stage of International Application No. PCT/US2009/061246 filed Oct. 20, 2009, which claims the benefit of priority of U.S. Provisional Application No. 61/107,438, filed Oct. 22, 2008, the contents of each of which are incorporated herein by reference in their entirety. Work on this invention was also supported by grants from the Cystic Fibrosis Foundation.

This invention was made with government support under Grant No. R01-DK075309 awarded by National Institutes of Health. The government has certain rights in the invention.

BACKGROUND OF THE INVENTION

CFTR (Cystic Fibrosis Transmembrane Conductance Regulator) is the target of mutations that cause cystic fibrosis (CF). CF is characterized by abnormal endocrine and exocrine gland function. In CF, unusually thick mucus leads to chronic pulmonary disease and respiratory infections, insufficient pancreatic and digestive function, and abnormally concentrated sweat. Seventy percent of the mutant CFTR alleles in the Caucasian population result from deletion of phenylalanine at position 508 (ΔF508-CFTR), the result of a three base pair deletion in the genetic code. Other mutations have also been described, e.g., a glycine to aspartate substitution at position 551 (G551D-CFTR) occurs in approximately 1% of cystic fibrosis patients.

The ΔF508-CFTR mutation results in a CFTR protein capable of conducting chloride, but absent from the plasma membrane because of aberrant intracellular processing. Under usual conditions (37° C.), the ΔF508-CFTR protein is retained in the endoplasmic reticulum (ER), by prolonged association with the ER chaperones, including calnexin and hsp70. Over expression of ΔF508-CFTR can result in ΔF508-CFTR protein appearing at the cell surface, and this protein is functional once it reaches the cell surface. The ΔF508-CFTR "trafficking" block is also reversible by incubation of cultured CF epithelial cells at reduced temperatures (25-27° C.). Lowered temperature results in the appearance of CFTR protein and channel activity at the cell surface, suggesting an intrinsic thermodynamic instability in ΔF508-CFTR at 37° C. that leads to recognition of the mutant protein by the ER quality control mechanism, prevents further trafficking, and results in protein degradation. Chemical chaperones are currently being developed to restore the folding of ΔF508-CFTR. However, when ΔF508-CFTR is expressed at the cell-surface following treatment, CAL (also known as CFTR-associated ligand, PIST, GOPC, ROS, and FIG) directs the lysosomal degradation of CFTR in a dose-dependent fashion and reduces the amount of CFTR found at the cell surface. Conversely, NHERF1 and NHERF2 functionally stabilize CFTR. Consistent with this role of CAL, RNA interference targeting of endogenous CAL also increases cell-surface expression of the disease-associated ΔF508-CFTR mutant and enhances transepithelial chloride currents in a polarized human patient bronchial epithelial cell line (Wolde, et al. (2007) J. Biol. Chem. 282:8099-8109).

Current treatments for cystic fibrosis generally focus on controlling infection through antibiotic therapy and promoting mucus clearance by use of postural drainage and chest percussion. However, even with such treatments, frequent hospitalization is often required as the disease progresses. New therapies designed to increase chloride ion conductance in airway epithelial cells have been proposed, and restoration of the expression of functional CFTR at the cell surface is considered a major therapeutic goal in the treatment of cystic fibrosis, a disease that affects ~30,000 patients in the U.S., and ~70,000 patients worldwide. Indeed, screening assays have been described for identifying agents that modify or restore cell surface expression of mutant CFTR proteins. However, only a limited number of "corrector" drugs has been described for the treatment of CF. In addition, U.S. Patent Application No. 20050282743 discloses reagents and methods for inhibiting interactions between proteins in cells, particularly interactions between a PDZ protein such as PIST and a PL protein such as wild-type CFTR. However, no high-affinity and selective inhibitor compounds have been identified for PIST, nor have PIST reporter sequences been identified that would permit small-molecule screening, nor have any such compounds been shown to have efficacy in stabilizing mutant, degradation-prone CFTR. Accordingly, improvements are needed in the treatment of cystic fibrosis. The present invention fulfills this need and further provides other related advantages.

SUMMARY OF THE INVENTION

The present invention features methods for increasing cell surface expression of a degradation-prone Cystic Fibrosis Transmembrane Conductance Regulator (CFTR) protein and a method of preventing or treating CF in a subject in need of treatment. The methods of the invention employ an agent that selectively inhibits the interaction between the degradation-prone CFTR and CFTR-Associated Ligand (CAL) thereby increasing cell surface expression of the degradation-prone CFTR protein. In one embodiment, the degradation-prone CFTR is ΔF508 CFTR or R1066C CFTR. In other embodiments of the invention, the agent is a peptide or peptidomimetic of 6 to 20 residues in length. In certain embodiments, the peptide comprises the amino acid sequence of SEQ ID NO:1 or a derivative thereof. In particular embodiments, the peptide is listed in Table 1. In another embodiment, the peptidomimetic is a mimetic of the amino acid sequence of SEQ ID NO:1. In a further embodiment, the peptidomimetic is listed in Table 2.

Peptides, derivatives, peptidomimetic, as well as compositions containing the same are also provided.

DETAILED DESCRIPTION OF THE INVENTION

Novel inhibitors have now been identified that block the interaction or binding of CFTR with the CAL PDZ binding site by competitive displacement. By inhibiting this interaction with CAL, degradation-prone CFTR proteins are stabilized and the amount of CFTR protein at the cell surface is effectively increased. Indeed, representative peptide and peptidomimetic CAL inhibitors were shown to increase the apical cell-surface expression and transepithelial chloride efflux of the most common CFTR mutation associated with CF. Accordingly, inhibitors of the present invention find application in increasing the cell surface expression of degradation-prone CFTR proteins and in the treatment for CF. As used herein, "cell surface expression" of a CFTR protein refers to CFTR protein which has been transported to the surface of a cell. In this regard, an agent that increases the cell surface expression of a CFTR protein refers to an agent that increases the amount of CFTR protein, which is present or detected at the plasma membrane of a cell, as compared to a cell which is not contacted with the agent.

Genetic, biochemical, and cell biological studies have revealed a complex network of protein-protein interactions that are required for correct CFTR trafficking, including a number of PDZ (PSD-95, discs-large, zonula occludens-1) proteins, which act as adaptor molecules, coupling CFTR to other components of the trafficking and localization machinery, and to other transmembrane channels and receptors (Kunzelmann (2001) News Physiol. Sci. 16:167-170; Guggino & Stanton (2006) Nat. Rev. Mol. Cell. Biol. 7:426-436). Class I PDZ domains typically recognize C-terminal binding motifs characterized by the sequence—(Ser/Thr)-X-Φ-COOH (where Φ represents a hydrophobic side chain, and X represents any amino acid) (Harris & Lim (2001) J. Cell Sci. 114:3219-3231; Brône & Eggermont (2005) Am. J. Physiol. 288:C20-C29). The cytoplasmic C-terminus of CFTR satisfies the class I PDZ binding motif, ending in the sequence—Thr-Arg-Leu (Hall, et al. (1998) Proc. Natl. Acad. Sci. USA 95:8496-8501; Short, et al. (1998) J. Biol. Chem. 273:19797-19801; Wang, et al. (1998) FEBS Lett. 427:103-108) and it has been demonstrated that CFTR C-terminal PDZ-binding motif controls retention of the protein at the apical membrane and modulates its endocytic recycling (Moyer, et al. (2000) J. Biol. Chem. 275:27069-27074; Swiatecka-Urban, et al. (2002) J. Biol. Chem. 277:40099-40105). PDZ proteins that have been shown to bind or interact with CFTR include NHERF1 (Na+/H+ exchanger regulatory factor 1; also known as EBP50), NHERF2 (Na+/H+ exchanger regulatory factor 2, also known as E3KARP), NHERF3 (Na+/H+ exchanger regulatory factor 3, also known as CAP70, PDZK1, or NaPi CAP-1), NHERF4 (Na+/H+ exchanger regulatory factor 4, also known as IKEPP or NaPi CAP-2), and CAL (CFTR-associated ligand; also known as PIST, GOPC, and FIG; GENBANK Accession Nos. NP_065132 and NP_001017408, incorporated herein by reference) (Guggino & Stanton (2006) supra; Li & Naren (2005) Pharmacol. Ther. 108:208-223). Of these proteins, CAL has been shown to reduce the levels of recombinant wild-type CFTR found in whole cell lysates and at the cell surface, whereas overexpression of NHERF1 together with CAL can block this effect on both wild-type and ΔF508-CFTR (Cheng, et al. (2002) J. Biol. Chem. 277:3520-3529; Guerra, et al. (2005) J. Biol. Chem. 280:40925-40933). Moreover, RNAi targeting of endogenous CAL specifically increases cell surface expression of the ΔF508-CFTR mutant protein and enhances transepithelial chloride currents in a polarized human patient bronchial epithelial cell line (Wolde, et al. (2007) J. Biol. Chem. 282:8099-8109). These data indicate that the PDZ proteins which interact with CFTR have opposing functions. Thus, targeting the interaction of CAL with CFTR can stabilize a mutant CFTR protein and facilitate cell surface expression of the same.

The CFTR protein and mutants thereof are well-known in the art and wild-type human CFTR is disclosed in GENBANK Accession No. NP_000483, incorporated herein by reference. Misfolding of mutant CFTR proteins has been shown to dramatically augment the ubiquitination susceptibility of the protein in post-Golgi compartments (Swiatecka-Urban, et al. (2005) J. Biol. Chem. 280:36762). Thus, for the purposes of the present invention, the term "degradation-prone" when used as a modifier of a CFTR protein, refers to a mutant CFTR protein that exhibits an increased rate of degradation following initial trafficking to the cell surface and a decrease in the amount of CFTR protein present at the cell surface (i.e., plasma membrane). Examples of degradation-prone CFTR proteins include, but are not limited to ΔF508 CFTR and Δ70F CFTR (see Sharma, et al. (2004) J. Cell Biol. 164:923). Other degradation-prone CFTR proteins are known in the art and/or can be identified by routine experimentation. For example, the rate or amount of transport of CFTR protein from the cell surface can be determined by detecting the amount of complex-glycosylated CFTR protein present at the cell surface, in endoplasmic vesicles and/or in lysosomes using methods such as cell surface immunoprecipitation or biotinylation or cell immunocytochemistry with an antibody specific for CFTR protein. Additional methods, both in vivo and in vitro, are known in the art that can be used for detecting an increase or decrease in cell surface expression of a CFTR protein.

Because PDZ proteins share overlapping specificities, particular embodiments of this invention embrace inhibitory agents that selectively block the interaction or binding between a degradation-prone CFTR and CAL. As used herein, a "selective inhibitor of the CFTR and CAL interaction" or "an agent that selectively inhibits the interaction between the degradation-prone CFTR and CAL" is any molecular species that is an inhibitor of the CFTR and CAL interaction but which fails to inhibit, or inhibits to a substantially lesser degree the interaction between CFTR and proteins that stabilize degradation-prone CFTR, e.g., NHERF1 AND NHERF2. Methods for assessing the selectively of an inhibitor of the CFTR and CAL interaction are disclosed herein and can be carried out in in vitro or in vivo assays.

By way of illustration, libraries of agents were screened for the ability to increase the amount of ΔF508 CFTR at the apical membrane and to increase the CFTR-mediated chloride efflux across monolayers of CFBE41O-cells. The magnitude of the functional rescue of the mutant CFTR protein correlated with the selectivity of the agent for CAL versus NHERF1 and NHERF2, namely, the more selective the agent for the CAL binding site, the more effective the agent was at enhancing chloride efflux.

Accordingly, the present invention features compositions and methods for facilitating the cell surface expression of mutant CFTR by selectively blocking the interaction between a degradation-prone CFTR and CAL. Agents of the present invention can be any molecular species, with particular embodiments embracing peptides or mimetics thereof.

As used herein, the term "peptide" denotes an amino acid polymer that is composed of at least two amino acids covalently linked by an amide bond. Peptides of the present invention are desirably 6 to 20 residues in length, or more desirably 7 to 15 residues in length. In certain embodiments, a selective inhibitor of the CFTR and CAL interaction is a 6 to 20 residue peptide containing the amino acid sequence $Xaa_1$-$Xaa_2$-$Xaa_3$-$Xaa_4$-$Xaa_5$-Ile (SEQ ID NO:1), wherein $Xaa_1$ is Met, Phe or Trp; $Xaa_2$ is Gln, Pro, or Phe; $Xaa_3$ is Ser or Thr; $Xaa_4$ is Ser or Thr; and $Xaa_5$ is Lys or Ile. In certain embodiments of the present invention, a selective inhibitor of the CFTR and CAL interaction is a peptide having an amino acid sequence as listed in Table 1.

TABLE 1

| Peptide Designation | Peptide Sequence | SEQ ID NO: |
|---|---|---|
| PRC 01 | CANGLMQTSKI | 2 |
| PRC 02 | CGLMQTSKI | 3 |
| PRC 03 | CFFSTII | 4 |
| PRC 04 | CFFTSII | 5 |
| PRC 05 | CMQTSII | 6 |
| PRC 06 | CMQTSKI | 7 |
| PRC 07 | CWQTSII | 8 |
| PRC 08 | CWPTSII | 9 |
| PRC 09 | CTWQTSII | 10 |
| PRC 10 | CKWQTSII | 11 |
| PRC 11 | PHWQTSII | 12 |
| PRC 12 | FHWQTSII | 13 |

TABLE 1-continued

| Peptide Designation | Peptide Sequence | SEQ ID NO: |
|---|---|---|
| PRC 13 | SRWQTSII | 14 |
| PRC 17 | CANSRWQTSII | 15 |
| PRC 25 | GLWPTSII | 16 |
| PRC 26 | SRWPTSII | 17 |
| PRC 27 | FPWPTSII | 18 |
| PRC 30 | *FITC-ANSRWPTSII | 19 |
| PRC 36 | ANSRWPTSII | 20 |

FITC = fluorescein.

In accordance with the present invention, derivatives of the peptides of the invention are also provided. As used herein, a peptide derivative is a molecule which retains the primary amino acids of the peptide, however, the N-terminus, C-terminus, and/or one or more of the side chains of the amino acids therein have been chemically altered or derivatized. Such derivatized peptides include, for example, naturally occurring amino acid derivatives, for example, 4-hydroxyproline for proline, 5-hydroxylysine for lysine, homoserine for serine, ornithine for lysine, and the like. Other derivatives or modifications include, e.g., a label, such as fluorescein or tetramethylrhodamine; or one or more post-translational modifications such as acetylation, amidation, formylation, hydroxylation, methylation, phosphorylation, sulfatation, glycosylation, or lipidation. Indeed, certain chemical modifications, in particular N-terminal glycosylation, have been shown to increase the stability of peptides in human serum (Powell et al. (1993) *Pharma. Res.* 10:1268-1273). Peptide derivatives also include those with increased membrane permeability obtained by N-myristoylation (Brand, et al. (1996) *Am. J. Physiol. Cell. Physiol.* 270:C1362-C1369). An exemplary peptide derivative is provided in SEQ ID NO:19 (Table 1).

In addition, a peptide derivative of the invention can include a cell-penetrating sequence which facilitates, enhances, or increases the transmembrane transport or intracellular delivery of the peptide into a cell. For example, a variety of proteins, including the HIV-1 Tat transcription factor, *Drosophila* Antennapedia transcription factor, as well as the herpes simplex virus VP22 protein have been shown to facilitate transport of proteins into the cell (Wadia and Dowdy (2002) *Curr. Opin. Biotechnol.* 13:52-56). Further, an arginine-rich peptide (Futaki (2002) *Int. J. Pharm.* 245:1-7), a polylysine peptide containing Tat PTD (Hashida, et al. (2004) *Br. J. Cancer* 90(6):1252-8), Pep-1 (Deshayes, et al. (2004) *Biochemistry* 43(6):1449-57) or an HSP70 protein or fragment thereof (WO 00/31113) is suitable for enhancing intracellular delivery of a peptide or peptidomimetic of the invention into the cell. An exemplary cell penetrating peptide is shown in Table 2 and provided as SEQ ID NO:30.

While a peptide of the invention can be derivatized with by one of the above indicated modifications, it is understood that a peptide of this invention may contain more than one of the above described modifications within the same peptide.

As indicated, the present invention also encompasses peptidomimetics of the peptides disclosed herein. Peptidomimetics refer to a synthetic chemical compound which has substantially the same structural and/or functional characteristics of the peptides of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the activity of the mimetic. Routine testing can be used to determine whether a mimetic has the requisite activity, e.g., that it can inhibit the interaction between CFTR and CAL. The phrase "substantially the same," when used in reference to a mimetic or peptidomimetic, means that the mimetic or peptidomimetic has one or more activities or functions of the referenced molecule, e.g., selective inhibition of the CAL and CFTR interaction.

There are clear advantages for using a mimetic of a given peptide. For example, there are considerable cost savings and improved patient compliance associated with peptidomimetics, since they can be administered orally compared with parenteral administration for peptides. Furthermore, peptidomimetics are much cheaper to produce than peptides.

Thus, peptides described above have utility in the development of such small chemical compounds with similar biological activities and therefore with similar therapeutic utilities. The techniques of developing peptidomimetics are conventional. For example, peptide bonds can be replaced by non-peptide bonds or non-natural amino acids that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to a CAL protein, by NMR spectroscopy, crystallography and/or computer-aided molecular modeling. These techniques aid in the development of novel compositions of higher potency and/or greater bioavailability and/or greater stability than the original peptide (Dean (1994) *BioEssays* 16:683-687; Cohen & Shatzmiller (1993) *J. Mol. Graph.* 11:166-173; Wiley & Rich (1993) *Med. Res. Rev.* 13:327-384; Moore (1994) *Trends Pharmacol. Sci.* 15:124-129; Hruby (1993) *Biopolymers* 33:1073-1082; Bugg, et al. (1993) *Sci. Am.* 269:92-98). Once a potential peptidomimetic compound is identified, it may be synthesized and assayed using an assay described herein or any other appropriate assay for monitoring cell surface expression of CFTR.

It will be readily apparent to one skilled in the art that a peptidomimetic can be generated from any of the peptides described herein. It will furthermore be apparent that the peptidomimetics of this invention can be further used for the development of even more potent non-peptidic compounds, in addition to their utility as therapeutic compounds.

Peptide mimetic compositions can contain any combination of non-natural structural components, which are typically from three structural groups: residue linkage groups other than the natural amide bond ("peptide bond") linkages; non-natural residues in place of naturally occurring amino acid residues; residues which induce secondary structural mimicry, i.e., induce or stabilize a secondary structure, e.g., a beta turn, gamma turn, beta sheet, alpha helix conformation, and the like; or other changes which confer resistance to proteolysis. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins,* 7:267-357, "Peptide and Backbone Modifications," Marcel Decker, N.Y.).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues are mimetics of aromatic amino acids include, for example, D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenyl-phenylalanine; and D- or L-2-indole (alkyl)alanines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic ring include, for example, thiazolyl, thiophenyl, pyrazolyl, benzimidazolyl, naphthyl, furanyl, pyrrolyl, and pyridyl aromatic rings.

Cyclic peptides or cyclized residue side chains also decrease susceptibility of a peptide to proteolysis by exopeptidases or endopeptidases. Thus, certain embodiments embrace a peptidomimetic of the peptides disclosed herein, whereby one or more amino acid residue side chains are cyclized according to conventional methods.

Mimetics of acidic amino acids can be generated by substitution with non-carboxylate amino acids while maintaining a negative charge; (phosphono)alanine; and sulfated threonine. Carboxyl side groups (e.g., aspartyl or glutamyl) can also be selectively modified by reaction with carbodiimides (R'—N—C—N—R') including, for example, 1-cyclohexyl-3(2-morpholinyl-(4-ethyl) carbodiimide or 1-ethyl-3 (4-azonia-4,4-dimetholpentyl) carbodiimide. Aspartyl or glutamyl groups can also be converted to asparaginyl and glutaminyl groups by reaction with ammonium ions.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Methionine mimetics can be generated by reaction with methionine sulfoxide. Proline mimetics of include, for example, pipecolic acid, thiazolidine carboxylic acid, dehydroproline, 3- or 4-methylproline, and 3,3,-dimethylproline.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form.

As will be appreciated by one skilled in the art, the peptidomimetics of the present invention can also include one or more of the modifications described herein for derivatized peptides, e.g., a label, one or more post-translational modifications, or cell-penetrating sequence.

As with peptides of the invention, peptidomimetics are desirably 6 to 20 residues in length, or more desirably to 15 residues in length. In certain embodiments, a selective inhibitor of the CFTR and CAL interaction is a 6 to 20 residue peptidomimetic based on the amino acid sequence of SEQ ID NO:1. In certain embodiments of the present invention, a selective inhibitor of the CFTR and CAL interaction is a peptidomimetic listed in Table 2.

TABLE 2

| Peptide Designation | Peptide Sequence | SEQ ID NO: |
|---|---|---|
| PRC 21 | WrFK(K-FITC)-ANSRWPTSII | 21 |
| PRC 23 | WrFKK-ANSRWPTSII | 22 |
| PRC 29 | WrFK(K-ROX)-ANSRWPTSII | 23 |
| PRC 37 | pneaWPTSII | 24 |
| B1 | fNaRWQTSII | 25 |
| B2 | fNSRWQTSII | 26 |
| B3 | knSRWQTSII | 27 |
| B4 | pnSRWQTSII | 28 |
| A6 | AnSRWQTSII | 29 |

Lower-case = D-amino acids;
FITC = fluorescein;
ROX = 6-carboxy-X-rhodamine.
Underlined residues indicate cyclized side chains.
WrFKK (SEQ ID NO: 30) is a cell penetrating peptide.

Also included with the scope of the invention are peptides and peptidomimetics that are substantially identical to a sequence set forth herein, in particular SEQ ID NO:1. The term "substantially identical," when used in reference to a peptide or peptidomimetic, means that the sequence has at least 75% or more identity to a reference sequence (e.g., 80%, 85%, 90%, 95%, 96%, 97%, 98%, 99%). The length of comparison sequences will generally be at least 5 amino acids, but typically more, at least 6 to 10, 7 to 15, or 8 to 20 residues. In one aspect, the identity is over a defined sequence region, e.g., the amino or carboxy terminal 3 to 5 residues.

The peptides, derivatives and peptidomimetics can be produced and isolated using any method known in the art. Peptides can be synthesized, whole or in part, using chemical methods known in the art (see, e.g., Caruthers (1980) *Nucleic Acids Res. Symp. Ser.* 215-223; Horn (1980) *Nucleic Acids Res. Symp. Ser.* 225-232; and Banga (1995) *Therapeutic Peptides and Proteins, Formulation, Processing and Delivery Systems,* Technomic Publishing Co., Lancaster, Pa.). Peptide synthesis can be performed using various solid-phase techniques (see, e.g., Roberge (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the manufacturer's instructions.

Individual synthetic residues and peptides incorporating mimetics can be synthesized using a variety of procedures and methodologies known in the art (see, e.g., *Organic Syntheses Collective Volumes,* Gilman, et al. (Eds) John Wiley & Sons, Inc., NY). Peptides and peptide mimetics can also be synthesized using combinatorial methodologies. Techniques for generating peptide and peptidomimetic libraries are well-known, and include, for example, multipin, tea bag, and split-couple-mix techniques (see, for example, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; and Ostresh (1996) *Methods Enzymol.* 267:220-234). Modified peptides can be further produced by chemical modification methods (see, for example, Belousov (1997) *Nucleic*

*Acids Res.* 25:3440-3444; Frenkel (1995) *Free Radic. Biol. Med.* 19:373-380; and Blommers (1994) *Biochemistry* 33:7886-7896).

Alternatively, peptides of this invention can be prepared in recombinant protein systems using polynucleotide sequences encoding the peptides. By way of illustration, a nucleic acid molecule encoding a peptide of the invention is introduced into a host cell, such as bacteria, yeast or mammalian cell, under conditions suitable for expression of the peptide, and the peptide is purified or isolated using methods known in the art. See, e.g., Deutscher et al. (1990) *Guide to Protein Purification: Methods in Enzymology* Vol. 182, Academic Press.

It is contemplated that the peptides and mimetics disclosed herein can be used as lead compounds for the design and synthesis of compounds with improved efficacy, clearance, half-lives, and the like. One approach includes structure-activity relationship (SAR) analysis (e.g., NMR analysis) to determine specific binding interactions between the agent and CAL or CFTR to facilitate the development of more efficacious agents. Agents identified in such SAR analysis or from agent libraries can then be screened for their ability to increase cell surface expression of CFTR.

In this regard, the present invention also relates to a method for identifying an agent for which facilitates cell surface expression of a degradation-prone CFTR. The method of the invention involves contacting CAL with a test agent under conditions allowing an interaction between the agent and CAL, and determining whether the agent competitively displaces binding of a degradation-prone CFTR to CAL. Particular degradation-prone CFTRs that can be used include, but are not limited to, ΔF508 and R1066C.

In one embodiment, the method is performed in vivo. Various detection methods can be employed to determine whether the agent displaces CFTR from CAL. For example, displacement can be based on detecting an increase in an amount of CFTR protein on the cell surface, immunostaining with a specific antibody (e.g., anti-CFTR, M3A7), or direct visualization (e.g., a CFTR-GFP fusion). Additional methods useful for determining whether there is an increase in cell surface protein included cell panning. In cell panning assays, plates are coated with an antibody that binds to the cell surface protein. The number of cells that binds to the antibody coated plate corresponds to an amount of protein on the cell surface.

In another embodiment, the method is performed in vitro. In accordance with this embodiment, a combination of peptide-array screening and fluorescence polarization is used to identify agents that bind to an isolated, recombinant CAL PZD domain. For example, it contemplated that the high-affinity CAL-binding peptides disclosed herein can be use as reporters for small-molecule screening assays, wherein the small molecules compete for binding to the CAL PZD domain. The ability to target PDZ proteins selectively, using a combination of peptide-array screening and fluorescence-polarization assays on purified, recombinant PDZ domains, represents a novel achievement, due to the bi-directional promiscuity of PDZ:protein interactions. Since PDZ proteins are implicated in the trafficking and intracellular localization of many disease-related receptors, selective targeting may provide an important tool for identifying additional PDZ-based therapeutics.

In so far as it is desirable that the agent selectively inhibit the interaction between CAL and CFTR, a further embodiment of this invention embraces contacting NHERF1 and/or NHERF2 with an identified inhibitor of the CAL and CFTR interaction and determining whether the agent competitively displaces binding to NHERF1 and/or NHERF2. Agents that fail to inhibit, or inhibit to a substantially lesser degree the interaction between CFTR and NHERF1 or NHERF2 as compared to CAL, would be considered selective.

Agents which can be screened in accordance with the methods disclosed herein can be from any chemical class including peptides, antibodies, small organic molecules, carbohydrates, etc.

Agents specifically disclosed herein, as well as derivatives, and peptidomimetics of said agents and agents identified by design and/or screening assays find application in increasing in the cell surface expression of degradation-prone CFTR proteins and in the treatment of CF. Thus, methods for increasing the cell surface expression of a degradation-prone CFTR and treating cystic fibrosis are also provided by this invention.

In accordance with one embodiment, the cell surface expression of a degradation-prone CFTR protein is enhanced or increased by contacting a cell expressing a degradation-prone CFTR with an agent that decreases or inhibits the interaction between the CFTR protein and CAL so that the cell surface expression of the CFTR protein is increased or enhanced. Desirably, the agent is administered in an amount that effectively stabilizes the degradation-prone CFTR protein and increases the amount of said CFTR protein present or detectable at the cell surface by at least 60%, 70%, 80%, 90%, 95%, 99% or 100% as compared to cells not contacted with the agent. Any cell can be employed in this method of the invention so long as it expresses a degradation-prone CFTR. Specific examples of such cells include, but are not limited to, primary cells of a subject with CF or cultured airway epithelial cell lines derived from a CF patient's bronchial epithelium (e.g., CFBE41O-). It is contemplated that this method of the invention can be used to increase cell surface expression of a degradation-prone CFTR protein in a human subject as well as increase the cell surface expression of a degradation-prone CFTR protein in an isolated cell or cell culture to, e.g., study the transport and/or activity of the mutant protein at the cell surface.

In another embodiment, a subject with CF or at risk of CF is treated with one or more the agents of the invention. In accordance with this embodiment, an effective amount of an agent that selectively inhibits the interaction between a degradation-prone CFTR and CAL is administered to a subject in need of treatment thereby preventing or treating the subject's cystic fibrosis. Subjects benefiting from treatment with an agent of the invention include subjects confirmed as having CF, subjects suspected of having CF, or subjects at risk of having CF (e.g., subjects with a family history). In one aspect, the subject expresses a degradation-prone CFTR, such as ΔF508 or R1066C CFTR. Other CFTR mutant sequences are also known in the art including, for example, ΔI507, N1303K, S549I, S549R, A559T, H139R, G149R, D192G, R258G, S949L, H949Y, H1054D, G1061R, L1065P, R1066C, R1066H, R1066L, Q1071P, L 1077P, H1085R, W1098R, M1101K, M1101R.

Successful clinical use of a selective inhibitor of the invention can be determined by the skilled clinician based upon routine clinical practice, e.g., by monitoring frequency of respiratory infections and/or coughing; or changes in breathing, abdominal pain, appetite, and/or growth according to methods known in the art.

Agents disclosed herein can be employed as isolated molecules (i.e., isolated peptides, derivatives, or peptidomimetics), or in the case of peptides, be expressed from nucleic acids encoding said peptides. Such nucleic acids can, if desired, be naked or be in a carrier suitable for passing through a cell membrane (e.g., DNA-liposome complex), contained in a vector (e.g., plasmid, retroviral vector, lentiviral, adenoviral or adeno-associated viral vectors and the like), or linked to inert beads or other heterologous domains (e.g., antibodies, biotin, streptavidin, lectins, etc.), or other appropriate compositions. Thus, both viral and non-viral means of nucleic acid delivery can be achieved and are contemplated. Desirably, a vector used in accordance with the invention provides all the necessary control sequences to facilitate expression of the peptide. Such expression control sequences can include but are not limited to promoter sequences, enhancer sequences, etc. Such expression control sequences, vectors and the like are well-known and routinely employed by those skilled in the art.

For example, when using adenovirus expression vectors, the nucleic acid molecule encoding a peptide can be ligated to an adenovirus transcription/translation control complex, e.g., the late promoter and tripartite leader sequence. Alternatively, the vaccinia virus 7.5K promoter can be used. (see e.g., Mackett, et al. (1982) *Proc. Natl. Acad. Sci. USA* 79:7415-7419; Mackett, et al. (1984) *J. Virol.* 49:857-864; Panicali, et al. (1982) *Proc. Natl. Acad. Sci. USA* 79:4927-4931). Mammalian expression systems further include vectors specifically designed for "gene therapy" methods including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979) and retroviral vectors (U.S. Pat. Nos. 5,624,820, 5,693,508 and 5,674,703 and WIPO publications WO 92/05266 and WO 92/14829).

Moreover, agents of the invention can be combined with other agents employed in the treatment of CF, including molecules which ameliorate the signs or symptoms of CF. Such agents include, but are not limited to, nonsteroidal anti-inflammatory drugs or steroids, such as ibuprofen for treating inflammation; pentoxifylline for decreasing inflammation; dornase alfa for treating airway blockage due to mucus buildup or certain flavones and isoflavones, which are capable of stimulating CFTR-mediated chloride transport in epithelial tissues in a cyclic-AMP independent manner (U.S. Pat. No. 6,329,422); 2,2-dimethyl butyric acid (U.S. Pat. No. 7,265,153); glycerol, acetic acid, butyric acid, D- or L-amino-n-butyric acid, alpha- or beta-amino-n-butyric acid, arginine butyrate or isobutyramide, all disclosed in U.S. Pat. Nos. 4,822,821 and 5,025,029; butyrin, 4-phenyl butyrate, phenylacetate, and phenoxy acetic acid, disclosed in U.S. Pat. No. 4,704,402, wherein in combination with one or more agents of this invention, an additive or synergistic effect is achieved.

For therapeutic use, agents of the invention (including nucleic acids encoding peptides) can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically including via inhalation, transdermally, orally, intranasally, intravaginally, or rectally according to standard medical practices.

The selected dosage level of an agent will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician having ordinary skill in the art can readily determine and prescribe the effective amount of the pharmaceutical composition required based upon the administration of similar compounds or experimental determination. For example, the physician could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The fact that other proteins destined for the intracellular transport pathway frequently exhibit transport delays due to mutations, or other factors, indicates that the cell-surface expression of such degradation-prone proteins may also be mediated by CAL. Thus, it is contemplated that the agents of this invention can also be used to induce or increase the cell surface expression of other degradation-prone proteins. Accordingly, physiological disorders associated with other degradation-prone proteins besides CFTR can similarly be treated using the methods disclosed herein. Physiological disorders associated with a degradation-prone protein that can be treated in a method of the invention include, for example, Stargardt's disease and particular types of macular dystrophy caused by mutations of the retinal rod transporter, ABC-R, resulting in deficiency of export.

The invention is described in greater detail by the following non-limiting examples.

EXAMPLE 1

Identification of Selective Inhibitors of the CAL and CFTR Interaction

Using peptide-array screening and fluorescence-polarization binding assays, a series of peptide sequences were identified that bind CAL progressively more tightly than CAL binds to CFTR, and that in parallel bind NHERF1 and NHERF2 progressively more weakly than these proteins bind to CFTR.

To test the ability of CAL inhibitors to rescue CFTR, cultured airway epithelial cells (cell line CFBE41o-, derived from a CF patient's Bronchial Epithelium) were grown on filters, permitting formation of polarized cell monolayers similar to those found in epithelial tissues.

The CFBE41o-cell line is well-recognized as an airway epithelial model system for the study of CF processes. These cells express the most common disease mutant associated with CF, ΔF508-CFTR, which is characterized by the loss of a single amino acid codon at position 508 of CFTR. Roughly 50% of CF patients are homozygous for ΔF508-CFTR, and another 40% are heterozygotes for this allele. Functional rescue of ΔF508-CFTR therefore has the potential to alleviate symptoms in up to 90% of CF patients. Although very little ΔF508-CFTR protein is synthesized in the absence of intervention, the protein itself retains some functional activity. If rescued and stabilized it can restore physiological CFTR activity, potentially reversing the processes that lead to chronic lung infection, and ultimately death, in most CF patients.

When introduced into CFBE41o-cells using commercial peptide transfection reagents, representative peptide and peptidomimetic compounds were able to increase the amount of ΔF508-CFTR protein at the apical membrane and to increase the CFTR-mediated chloride efflux across the monolayers. The magnitude of the functional rescue correlated with the selectivity of the peptides for CAL vs. NHERF1 and NHERF2; the more selective the peptide for the CAL binding site, the more effective it was at enhancing chloride efflux.

Furthermore, when used in combination with a compound that enhances the biosynthesis of ΔF508-CFTR (a "corrector"), the instant inhibitors showed an additive effect, comparable in magnitude to that of the corrector compound.

Although compounds have previously been designed to enhance the synthesis and/or chloride-channel activity of CFTR, the instant inhibitors were designed to stabilize mutant CFTR protein that has already been synthesized within the cell and successfully transported to the cell surface. The peptides and peptidomimetics disclosed herein provide a basis for further optimization of CAL inhibitor properties in terms of affinity and selectivity for CAL, in vivo proteolytic stability, cellular uptake, and ADME characteristics.

EXAMPLE 2

Assays for Assessing Activity of Selective Inhibitors

Agents of the present invention can be assayed for their ability to stimulate chloride transport in epithelial tissues. Such transport may result in secretion or absorption of chloride ions. The ability to stimulate chloride transport may be assessed using any of a variety of systems. For example, in vitro assays using a mammalian trachea or a cell line, such as the permanent airway cell line Calu-3 (ATCC Accession Number HTB55) may be employed. Alternatively, the ability to stimulate chloride transport may be evaluated within an in vivo assay employing a mammalian nasal epithelium. In general, the ability to stimulate chloride transport may be assessed by evaluating CFTR-mediated currents across a membrane by employing standard Ussing chamber (see Ussing & Zehrahn (1951) Acta. Physiol. Scand. 23:110-127) or nasal potential difference measurements (see Knowles, et al. (1995) Hum. Gene Therapy 6:445-455). Within such assays, an agent that stimulates a statistically significant increase in chloride transport at a concentration of about 1-300 μM is said to stimulate chloride transport.

Within one in vitro assay, the level of chloride transport may be evaluated using mammalian pulmonary cell lines, such as Calu-3 cells, or primary bovine tracheal cultures. In general, such assays employ cell monolayers, which may be prepared by standard cell culture techniques. Within such systems, CFTR-mediated chloride current may be monitored in an Ussing chamber using intact epithelia. Alternatively, chloride transport may be evaluated using epithelial tissue in which the basolateral membrane is permeabilized with *Staphylococcus aureus* α-toxin, and in which a chloride gradient is imposed across the apical membrane (see Illek, et al. (1996) *Am. J. Physiol.* 270:C265-75). In either system, chloride transport is evaluated in the presence and absence of a test agent, and those compounds that stimulate chloride may be used within the methods provided herein.

Within another in vitro assay for evaluating chloride transport, cells, such as NIH 3T3 fibroblasts, are transfected with a CFTR gene having a mutation associated with cystic fibrosis (e.g., ΔF508-CFTR) using well known techniques (see Anderson, et al. (1991) *Science* 25:679-682). The effect of an agent on chloride transport in such cells is then evaluated by monitoring CFTR-mediated currents using the patch clamp method (see Hamill, et al. (1981) *Pflugers Arch.* 391:85-100) with and without agent.

Alternatively, such assays may be performed using a mammalian trachea, such as a primary cow tracheal epithelium using the Ussing chamber technique as described above. Such assays are performed in the presence and absence of a test agent to identify agents that stimulate chloride transport.

What is claimed is:

1. An isolated peptide comprising $Xaa_1$-$Xaa_2$-$Xaa_3$-$Xaa_4$-$Xaa_5$-Ile (SEQ ID NO: 1), wherein $Xaa_1$ is Met or Trp; $Xaa_2$ is Gln, Pro, or Phe; $Xaa_3$ is Ser or Thr; $Xaa_4$ is Ser or Thr; and $Xaa_5$ is Lys or Ile, or a derivative or peptidomimetic thereof wherein the peptide, derivative or peptidomimetic is 6 to 20 residues in length.

2. An isolated peptide consisting of the sequence selected from the group of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

3. An isolated peptidomimetic consisting of the sequence selected from the group of SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29.

4. A pharmaceutical composition comprising the peptide of claim 1 in admixture with a pharmaceutically acceptable carrier.

5. A pharmaceutical composition comprising the peptide of claim 2 in admixture with a pharmaceutically acceptable carrier.

6. A pharmaceutical composition comprising the peptidomimetic of claim 3 in admixture with a pharmaceutically acceptable carrier.

* * * * *

UNITED STATES PATENT AND TRADEMARK OFFICE
CERTIFICATE OF CORRECTION

PATENT NO. : 8,415,292 B2  Page 1 of 1
APPLICATION NO. : 13/124470
DATED : April 9, 2013
INVENTOR(S) : Dean Madden It is certified that error appears in the above-identified patent and that said Letters Patent is hereby corrected as shown below:

On the Title Page, Item (75), delete "Boinguérin" and insert --Boisguérin--

Signed and Sealed this
Thirtieth Day of July, 2013

Teresa Stanek Rea
*Acting Director of the United States Patent and Trademark Office*

SEQUENCE LISTING

```
<160> NUMBER OF SEQ ID NOS: 30

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Met, Phe or Trp
<220> FEATURE:
<221> NAME/KEY: MISC_FEATURE
<222> LOCATION: (2)..(2)
```

```
<223> OTHER INFORMATION: Xaa denotes Gln, Pro, or Phe
<220> FEATURE:
<221> NAME/KEY: MISC_FEATURE
<222> LOCATION: (3)..(4)
<223> OTHER INFORMATION: Xaa independently denotes Ser or Thr
<220> FEATURE:
<221> NAME/KEY: MISC_FEATURE
<222> LOCATION: (5)..(5)
<223> OTHER INFORMATION: Xaa denotes Lys or Ile

<400> SEQUENCE: 1

Xaa Xaa Xaa Xaa Xaa Ile
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Cys Ala Asn Gly Leu Met Gln Thr Ser Lys Ile
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Cys Gly Leu Met Gln Thr Ser Lys Ile
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Cys Phe Phe Ser Thr Ile Ile
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Cys Phe Phe Thr Ser Ile Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Cys Met Gln Thr Ser Ile Ile
1               5
```

```
<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Cys Met Gln Thr Ser Lys Ile
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Cys Trp Gln Thr Ser Ile Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Cys Trp Pro Thr Ser Ile Ile
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Cys Thr Trp Gln Thr Ser Ile Ile
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Cys Lys Trp Gln Thr Ser Ile Ile
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Pro His Trp Gln Thr Ser Ile Ile
1               5

<210> SEQ ID NO 13
```

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Phe His Trp Gln Thr Ser Ile Ile
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Ser Arg Trp Gln Thr Ser Ile Ile
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide

<400> SEQUENCE: 15

Cys Ala Asn Ser Arg Trp Gln Thr Ser Ile Ile
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Gly Leu Trp Pro Thr Ser Ile Ile
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Ser Arg Trp Pro Thr Ser Ile Ile
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Phe Pro Trp Pro Thr Ser Ile Ile
1               5

<210> SEQ ID NO 19
<211> LENGTH: 10
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with fluorescein

<400> SEQUENCE: 19

Ala Asn Ser Arg Trp Pro Thr Ser Ile Ile
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Ala Asn Ser Arg Trp Pro Thr Ser Ile Ile
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue
<220> FEATURE:
<221> NAME/KEY: MISC_FEATURE
<222> LOCATION: (5)..(5)
<223> OTHER INFORMATION: Modified with fluorescein

<400> SEQUENCE: 21

Trp Arg Phe Lys Lys Ala Asn Ser Arg Trp Pro Thr Ser Ile Ile
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue

<400> SEQUENCE: 22

Trp Arg Phe Lys Lys Ala Asn Ser Arg Trp Pro Thr Ser Ile Ile
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue
<220> FEATURE:
<221> NAME/KEY: MISC_FEATURE
<222> LOCATION: (5)..(5)
<223> OTHER INFORMATION: Modified with 6-carboxy-X-rhodamine
```

```
<400> SEQUENCE: 23

Trp Arg Phe Lys Lys Ala Asn Ser Arg Trp Pro Thr Ser Ile Ile
1               5                   10                  15

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(4)
<223> OTHER INFORMATION: D-amino acid residue

<400> SEQUENCE: 24

Pro Asn Glu Ala Trp Pro Thr Ser Ile Ile
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (3)..(3)
<223> OTHER INFORMATION: D-amino acid residue

<400> SEQUENCE: 25

Phe Asn Ala Arg Trp Gln Thr Ser Ile Ile
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-amino acid residue

<400> SEQUENCE: 26

Phe Asn Ser Arg Trp Gln Thr Ser Ile Ile
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid residue

<400> SEQUENCE: 27

Lys Asn Ser Arg Trp Gln Thr Ser Ile Ile
1               5                   10

<210> SEQ ID NO 28
<211> LENGTH: 10
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid residue

<400> SEQUENCE: 28

Pro Asn Ser Arg Trp Gln Thr Ser Ile Ile
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue

<400> SEQUENCE: 29

Ala Asn Ser Arg Trp Gln Thr Ser Ile Ile
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue

<400> SEQUENCE: 30

Trp Arg Phe Lys Lys
1               5
```